(12) United States Patent
Schuele et al.

(10) Patent No.: US 8,076,094 B2
(45) Date of Patent: Dec. 13, 2011

(54) PHOSPHORYLATION OF HISTONE H3 AT THREONINE 11—A NOVEL EPIGENETIC MARK FOR TRANSCRIPTIONAL REGULATION

(75) Inventors: Roland Schuele, Weisweil (DE); Eric Metzger, Neuf-Brisach (FR)

(73) Assignee: Universitaetsklinixum Freiburg, Freiburg (DD)

( * ) Notice: Subject to any disclaimer, the term of this patent is extended or adjusted under 35 U.S.C. 154(b) by 0 days.

(21) Appl. No.: 12/669,294

(22) PCT Filed: May 27, 2008

(86) PCT No.: PCT/EP2008/004201
§ 371 (c)(1),
(2), (4) Date: Mar. 11, 2010

(87) PCT Pub. No.: WO2009/010121
PCT Pub. Date: Jan. 22, 2009

(65) Prior Publication Data
US 2010/0285026 A1 Nov. 11, 2010

(30) Foreign Application Priority Data
Jul. 16, 2007 (EP) .................... 07013919

(51) Int. Cl.
G01N 33/574 (2006.01)
G01N 33/53 (2006.01)
(52) U.S. Cl. ..................... 435/7.23; 435/7.21
(58) Field of Classification Search ........................ None
See application file for complete search history.

(56) References Cited

U.S. PATENT DOCUMENTS 7,767,411 B2 8/2010 Schuele et al.
2007/0196882 A1 8/2007 Schuele et al.

FOREIGN PATENT DOCUMENTS

EP 1 574 857 A1 9/2005

OTHER PUBLICATIONS

Metzger E et al: "A Novel Inducible Transactivation Domain in the Androgen Receptor: Implications for PRK in Prostate Cancer" EMBO Journal, Oxford University Press, Surrey, GB, vol. 22, No. 2, Jan. 15, 2003, pp. 270-280.
Zhu Yimin et al: "Signaling via a novel integral plasma membrane pool of a serine/threonine protein kinase PRK1 in mammalian cells." The FASEB Journal : Official Publication of the Federation of American Societies for Experimental Biology Nov. 2004, vol. 18, No. 14, Nov. 2004, pp. 1722-1724.
Preuss Ute et al: "Novel mitosis-specific phosphorylation of histone H3 at Thr11 mediated by Dlk/ZIP kinase." Nucleic Acids Research, vol. 31, No. 3, Feb. 1, 2003, pp. 878-885.
Nowak S J et al: "Phosphorylation of histone H3: a balancing act between chromosome condensation and transcriptional activation" Trends in Genetics, Elsevier Science Publishers B.V. Amsterdam, NL, vol. 20, No. 4, Apr. 2004, pp. 214-220.
Wissmann Melanie et al: "Cooperative demethylation by JMJD2C and LSD1 promotes androgen receptor-dependent gene expression" Nature Cell Biology, Macmillan Publishers, GB, vol. 9, No. 3, Mar. 2007, pp. 347-358.
Metzger et al: "Histone demethylation and androgen-dependent transcription" Current Opinion in Genetics & Development, Current Biology Ltd, XX, vol. 16, No. 5, Oct. 2006, pp. 513-517.
Kang Z et al: "Coregulator Recruitment and Histone Modifications in Transcriptional Regulation by the Androgen Receptor" Molecular Endocrinology, Baltimore, MD, US, vol. 18, No. 11, Nov. 2004, pp. 2633-2648.
Jia Li et al: "Locus-wide chromatin remodeling and enhanced androgen receptor-mediated transcription in recurrent prostate tumor cells" Molecular and Cellular Biology, vol. 26, No. 19, Oct. 2006, pp. 7331-7341.
Metzger Eric et al: "Phosphorylation of histone H3 at threonine 11 establishes a novel chromatin mark for transcriptional regulationx" Nature Cell Biology, vol. 10, No. 1, Jan. 2008, p. 53.
Croce L D et al: "Thrilling transcription through threonine phosphorylation" Nature Cell Biology 200801 GB, vol. 10, No. 1, Jan. 2008, pp. 5-6.
Shimada M et al: "Checkpoints meet the transcription at a novel histone milestone (H3-T11)" Cell Cycle 20080601 US, vol. 7, No. 11, Jun. 1, 2008, pp. 1555-1559.
Kang Z et al: "Involvement of Proteasome in the Dynamic Assembly of the Androgen receptor Transcription Complex", The Journal of Biological Chemistry, vol. 277, No. 50, pp. 48366-48371, 2002.
Metzger E et al: "LSD1 demethylates repressive histone marks to promote androgen-receptor-dependent transcription", Nature, vol. 437/Sep. 15, 2005, pp. 436-439.
O'Neill T et al: "Nucleosome Arrays Inhibit Both Initiation and Elongation of Transcripts by Bacteriophage T7 RNA Polymerase", J. Mol. Biol. (1992), 223, pp. 67-78.
Dong L et al: "Phosphorylation of protein kinase N by phosphoinositide-dependent protein kinase-1 mediates insulin signals to the actin cytoskeleton", PNAS, May 9, 2000, vol. 97, No. 10, pp. 5089-5094.
Strahl B et al: "The language of covalent histone modifications", Nature, vol. 403/Jan. 6, 2000, pp. 41-45.
Wiznerowicz M et al: "Conditional Suppression of Cellular Genes: Lentivirus Vector-Mediated Drug-Inducible RNA Interference", Journal of Virology, Aug. 2003, pp. 8957-8961.
Shang Y et al: "Formation of the Androgen Receptor Transcription Complex", Molecular Cell, vol. 9, pp. 601-610, 2002.
Phatnani H et al: "Phosphorylation and functions of the RNA polymerase II CTD", Genes & Development 20: 2922-2936, 2006.
Dai J et al: "The kinase haspin is required for mitotic histone H3 Thr 3 phosphorylation and normal metaphase chromosome alignment", Genes & Development 19: 472-488, 2005.
Kahl P. et al: "Androgen Receptor Coactivators Lysine-Specific Histone Demethylase 1 and Four and a Half LIM Domain Protein 2 Predict Risk of Prostate Cancer Recurrence", Cancer Res 2006, 66: (23), Dec. 1, 2006.

*Primary Examiner* — Misook Yu
*Assistant Examiner* — Lei Yao
(74) *Attorney, Agent, or Firm* — Greenblum & Bernstein, P.L.C.

(57) ABSTRACT

The present invention relates to a process for controlling at least one androgen receptor- (AR-) regulated mechanism in mammalian cells under histone-phosphorylating conditions, said process comprising allowing at least one inhibitor with specificity for at least one protein kinase C-related kinase (PRK) to act on said at least one PRK1 thereby modulating, preferably down-regulating, the activity of said at least one PRK and optionally blocking said at least one androgen receptor-regulated mechanism in said mammalian cells.

1 Claim, 7 Drawing Sheets

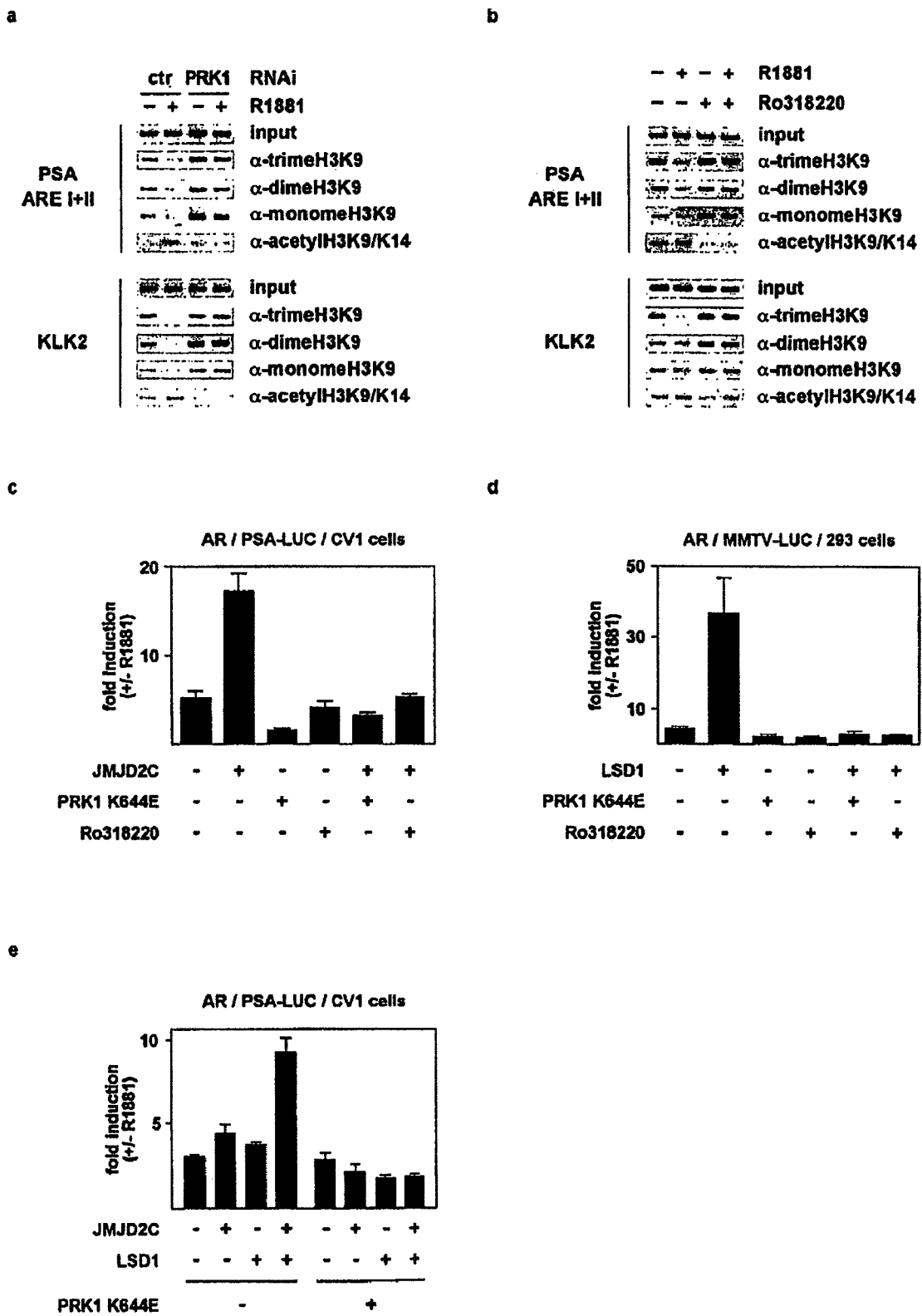

a b

PHOSPHORYLATION OF HISTONE H3 AT THREONINE 11—A NOVEL EPIGENETIC MARK FOR TRANSCRIPTIONAL REGULATION

BACKGROUND OF THE INVENTION

1. Field of the Invention

The present invention relates to a process for controlling androgen receptor-regulated mechanisms in mammalian cells under histone H3 at threonine 11- (H3T11-) phosphorylating conditions. Furthermore, the invention relates to a use of inhibitors having specificity for at least one protein kinase C-related kinase (PRK) for controlling androgen receptor-regulated mechanisms in mammalian cells.

2. Discussion of Background Information

Posttranslational modifications of histones such as methylation, acetylation and phoshorylation regulate chromatin structure and gene expression[1]. Threonine and serine residues are phosphorylated by specific kinases that stay under the control of signaling pathways. A phosphorylation of histone H3 at threonine 11 (H3T11) has not been linked to transcriptional regulation. The protein kinase C-related kinase 1 (PRK1)[2] has been shown to phosphorylate H3T11 upon ligand-dependent recruitment to androgen receptor (AR) target genes. H3T11 phosphorylation is an early event that precedes demethylation of mono-, di-, and trimethyl histone H3 at lysine 9 by JMJD2C and lysine specific demethylase 1 (LSD1). PRK1 is pivotal to AR function, since PRK1 knockdown by RNAi or PRK1 inhibition by treatment with Ro318220 impedes AR-dependent gene expression. Blocking PRK1 function abrogates androgen-induced phosphorylation of H3T11, but also blocks, in consequence, demethylation of mono-, di-, and trimethyl H3K9 as well as acetylation of histone H3 at lysines 9 and 14 (H3K9 and H3K14). Moreover, the presence of serine 5-phosphorylated RNA polymerrase II is no longer observed at AR target promoters. Thus, phosphorylation of H3T11 by PRK1 establishes a novel epigenetic mark for transcriptional activation, identifying PRK1 as a gatekeeper of AR-regulated gene expression. This pathway is of utmost importance since knockdown of PRK1 in prostate cancer cells inhibits androgen-induced transcriptional activation and tumor cell proliferation. Thus, our data suggest that specific gene regulation requires the assembly and coordinate action of kinases and demethylases. Furthermore, regulation of PRK1 activity alone or in combination with LSD1 and JMJD2C might be a promising therapeutic strategy to control AR activity in prostate cancer. Importantly, high PRK1 levels positively correlate with high Gleason scores of prostate carcinomas, allowing the present invention to be used in scoring prostate carcinomas.

The N-terminal tails of histones are subject to a plethora of posttranslational modifications such as acetylation, phosphorylation, and methylation by specific chromatin-modifying enzymes[1]. During gene expression, these modifications influence chromatin structure to facilitate the assembly of the RNA polymerase II transcription machinery[1,3]. Androgen receptor (AR)-dependent gene expression is characterized by epigenetic changes such as removal of repressive methyl marks from lysine 9 of histone H3 (H3K9)[4,5] and acetylation of lysines 9 and 14 of histone H3 (H3K9/K14)[6]. However, little is known about the upstream regulators that govern these epigenetic modifications. Since protein kinase C-related kinase 1 (PRK1) controls AR-dependent gene expression[2], we asked whether PRK1 signaling regulates epigenetic events at AR target genes.

Hence, it was an object of the present invention to identify further modulators of the AR-regulated gene expression and/or androgen-induced cell proliferation, particularly in mammalian cells.

Moreover, it was an object of the present invention to provide further modulators of histone modification, in particular of histone phosphorylation, methylation and acetylation.

Another object of the invention was to provide processes for controlling at least one androgen receptor-regulated mechanism in mammalian cells and for controlling the transcriptional AR activation induced by different routes.

A further object of the invention was to provide a new process for the prevention and/or treatment of prostate cancer.

Another object of the invention was to provide for the use of one or more than one inhibitor for the medicament manufacture, particularly for manufacturing a medicament for preventing and/or treating cancer, particularly prostate cancer.

Furthermore, it was an object of the invention to provide a means for scoring prostate cancers, particularly an assay system.

Finally, it was an object of the invention to provide an assay system for inhibitors having specificity for at least one PRK capable of blocking AR-induced prostate carcinoma cell proliferation.

SUMMARY OF THE INVENTION

The present invention relates to a process for controlling at least one androgen receptor- (AR-) regulated mechanism in mammalian cells under histone H3 at threonine 11- (H3T11-) phosphorylating conditions, said process comprising allowing at least one inhibitor with specificity for at least one protein kinase C-related kinase (PRK) to act on said at least one PRK, thereby modulating, preferably down-regulating, the activity of said at least one PRK and optionally blocking said at least one androgen receptor-regulated mechanism in said mammalian cells.

In one aspect of the above process, the at least one androgen receptor-regulated mechanism may be at least one mechanism selected from androgen receptor-controlled gene expression, androgen-induced cell proliferation, androgen-induced function of the prostate, androgen-induced build-up of muscles, androgen-induced build-up of the bone backbone, preferably androgen-induced control of the bone density, androgen-induced fertility, and androgen-induced hair growth of a mammal.

In another aspect, the at least one inhibitor may be a highly specific PRK inhibitor, preferably an inhibitor having a specificity of <100 nM, more preferably an inhibitor selected from RNAi's, antibodies, other peptides and dominant negative mutants of PRK's, most preferably an inhibitor selected from miRNA, siRNA, micro-RNA, shRNA, anti-PRKI antibodies and aptarners, as well as all chemical compounds known to a skilled person to be inhibitors of at least one PRK, specifically of PRK1.

In yet another aspect, the process may be performed in vitro, or the process may be performed in vivo.

In a still further aspect of the process, the at least one PRK may be selected from PRK1, PRK2, and PKNβ.

The invention also relates to the use of at least one inhibitor with specificity for at least one protein kinase C-related kinase (PRK) for the manufacture of a medicament for controlling at least one androgen receptor- (AR-) regulated mechanism in mammalian cells.

In one aspect of the above use, the at least one androgen receptor-regulated mechanism may be selected from androgen receptor-controlled gene expression, androgen-induced cell proliferation, androgen-induced function of the prostate, androgen-induced build-up of muscles, androgen-induced buildup of the bone backbone, preferably androgen-induced control of the bone density, androgen-induced fertility, and androgen-induced hair growth of a mammal.

In another aspect of the above use, the at least one inhibitor which is specific for at least one protein kinase C-related kinase may be selected from PRK1, PRK2, and PKNβ.

In a still further aspect, the use may be for the manufacture of a medicament for preventing and/or treating prostate cancer.

The invention also relates to a process for controlling the androgen dependent gene expression induced by a phosphorylation of histone H3 at threonine 11 (H3T11) in the presence of at least one protein kinase C-related kinase (PRK), said process comprising allowing at least one inhibitor with specificity for at least one protein kinase C-related kinase (PRK) to act on said at least one PRK, thereby modulating, preferably down-regulating, the activity of said at least one PRK and optionally blocking said androgen dependent gene expression; and/or to a process for controlling the androgen dependent gene expression induced by a demethylation of histone H3 at lysine 9 (H3K9) in the presence of at least one protein kinase C-related kinase (PRK), said process comprising allowing at least one inhibitor with specificity for at least one protein kinase C-related kinase (PRK) to act on said at least one PRK, thereby modulating, preferably down-regulating, the activity of said at least one PRK and optionally blocking said androgen dependent gene expression; and/or to a process for controlling the androgen dependent gene expression induced by an acetylation of histone H3 at lysine 9 (H3K9) and/or histone H3 at lysine 14 (H3K14) in the presence of at least one protein kinase C-related kinase (PRK), said process comprising allowing at least one inhibitor with specificity for at least one protein kinase C-related kinase (PRK) to act on said at least one PRK, thereby modulating, preferably down-regulating, the activity of said at least one PRK and optionally blocking said androgen dependent gene expression; and/or to a process for controlling the androgen dependent gene expression induced by a transition from the pre-initiation to the initiation complex which is characterized by a phosphorylation of RNA polymerase II at serine 5 in the C-terminal repeat domain (S5-pCDTpol II) in the presence of at least one protein kinase C-related kinase (PRK), said process comprising allowing at least one inhibitor with specificity for at least one protein kinase C-related kinase (PRK) to act on said at least one PRK, thereby modulating, preferably down-regulating, the activity of said at least one PRK and optionally blocking said androgen dependent gene expression.

In one aspect of the above processes, said modulation, preferably down-regulation, of a PRK activity may result in a modulation, preferably an inhibition, of the H3T11 phosphorylation and/or in a modulation, preferably an inhibition of the H3K9 demethylation, preferably of the trimethyl-H3K9 and/or of the dimethyl-H3K9 and/or of the monomethyl-H3K9, and/or in a modulation, preferably an inhibition, of the H3K9 and/or H3K14 acetylation.

In another aspect, said modulation, preferably down-regulation, of a PRK activity may result in a modulation, preferably inhibition, of H3T11 phosphorylation by at least one PRK and/or said modulation, preferably down-regulation, of a PRK activity may result in a modulation, preferably inhibition, of H3K9 demethylation by at least one histone demethylase and by at least one JMJD, each alone or both in combination, preferably by lysine specific demethylase (LSD1) and by JMJD2C, each alone or both in combination, and/or said down-regulation of a PRK activity may result in a modulation, preferably inhibition, of the H3K9 acetylation and/or H3K14 acetylation by acetylases, preferably P300/CBP or TIP60, and/or said down-regulation of a PRK activity may result in a modulation, preferably inhibition, of the transition from the pre-initiation to the initiation complex characterized by a phosphorylation of RNA polymerase II at serine 5 in the C-terminal repeat domain (S5-pCDTpol II) by CDK7.

In yet another aspect of the above processes, the processes may be performed in vitro, or they may be performed in vivo.

In a still further aspect, the at least one PRK may be selected from PRK1, PRK2, and PKNβ.

In another aspect of these processes, the at least one inhibitor may be a highly specific PRK inhibitor, preferably an inhibitor having a specificity of <100 nM, more preferably an inhibitor selected from RNAi's, antibodies, other peptides and dominant negative mutants of PRK's, most preferably an inhibitor selected from miRNA, siRNA, micro-RNA, shRNA, anti-PRK1 antibodies and aptamers, as well as all chemical compounds known to a skilled person to be inhibitors of at least one PRK, specifically of PRK1.

Additionally, the invention relates to a use of at least inhibitor with specificity for at least one protein kinase C-related kinase (PRK) for the manufacture of a medicament for controlling the androgen dependent gene expression induced by a phosphorylation of histone H3 at threonine 11 (H3T11) in the presence of at least one protein kinase C-related kinase (PRK); and/or to a use of at least inhibitor with specificity for at least one protein kinase C-related kinase (PRK) for the manufacture of a medicament for controlling the androgen dependent gene expression induced by a demethylation of histone H3 at lysine 9 (H3K9) in the presence of at least one protein kinase C-related kinase (PRK); and/or to a use of at least one inhibitor with specificity for at least one protein kinase C-related kinase (PRK) for the manufacture of a medicament for controlling the androgen dependent gene expression induced by an acetylation of histone H3 at lysine 9 (H3K9) and/or histone H3 at lysine 14 (H3K14) in the presence of at least protein kinase C-related kinase (PRK); and/or to a use of at least inhibitor with specificity for at least one protein kinase C-related kinase (PRK) for the manufacture of a medicament for controlling the androgen dependent gene expression induced by a transition from the pre-initiation to the initiation complex which is characterized by a phosphorylation of RNA polymerase II at serine 5 in the C-terminal repeat domain (S5-pCDTpol II) in the presence of at least one protein kinase C-related kinase (PRK).

In one aspect of the above uses, the androgen dependent gene expression control induced by a H3T11 phosphorylation may be a H3T11 phosphorylation by PRK and/or the androgen dependent gene expression induced by a H3K9 demethylation may be a H3K9 demethylation by histone demethylases and by JMJD's, each alone or both in combination, preferably by lysine specific demethylase (LSD1) and by JMJD2C, each alone or both in combination, and/or the androgen dependent gene expression induced by a H3K9 and/or H3K14 acetylation may be a H3K9 and/or H3K14 acetylation by acetylases, and/or the down-regulation of a PRK activity may result in a modulation, preferably inhibition, of the transition from the pre-initiation to the initiation complex characterized by a phosphorylation of RNA polymerase II at serine 5 in the C-terminal repeat domain (S5-pCDTpol II) by CDK7.

In another aspect, the at least one inhibitor may be specific for at least one protein kinase C-related kinase selected from PRK1, PRK2, and PKNβ.

In yet another aspect, the above uses may be for the manufacture of a medicament for preventing and/or treating prostate cancer.

The invention also relates to a process for the prevention and/or treatment of prostate cancer, said process comprising administering, to a plurality of mammalian cells in need thereof, including prostate cancer cells in need thereof, at least one inhibitor with specificity for at least one protein kinase C-related kinase, thereby modulating, preferably down-regulating, the phosphorylation of histone H3 at threonine 11 (H3T11) by said at least one PRK and/or modulating, preferably down-regulating, the demethylation of histone H3 at lysine 9 (H3K9) by at least one histone demethylase, preferably by lysine specific demethylase (LSD1) and/or by at least one JMJD, specifically by JMJD2C, each alone or both in combination, and/or modulating, preferably down-regulating, the acetylation of histone H3 at lysine 9 (H3K9) and/or of histone 3 at lysine 14 (H3K14) by at least one acetylase, and/or modulating, preferably down-regulating, the transition from the pre-initiation to the initiation complex by a phosphorylation of RNA polymerase II at serine 5 in the C-terminal repeat domain (S5-pCDTpol II) by CDK7.

The invention relates, too, to the use of at least one inhibitor with specificity for at least one protein kinase C-related kinase (PRK) for the manufacture of a medicament for the prevention and/or treatment of prostate cancer.

The invention also relates to the use of at least one antibody with specificity for at least one protein kinase C-related kinase (PRK) for the manufacture of a composition capable of scoring prostate carcinomas.

In addition, the invention relates to an assay system for screening inhibitors having specificity for at least one PRK capable of blocking AR-induced prostate carcinoma cell proliferation, said assay system comprising at least one PRK, an (optionally labelled) substrate [which, as the case may be, may also be a substrate with an antibody suitable for a detection], a phosphate-delivering component (as, for example, ATP) and suitable auxiliary substances as, for example one or more buffers and one or more pH-adjusting compound(s), etc.

Finally, the invention also relates to an assay system for scoring prostate carcinomas in a tissue sample, said assay system comprising a reagent for detecting the presence of PRK1. In a preferred embodiment of the assay system, said reagent is selected from the group consisting of an antibody against PRK1 and PCR primers.

BRIEF DESCRIPTION OF THE DRAWINGS

The invention is further in detail described by referring to the annexed Figures; however, the Figures are intended to show exemplarily preferred embodiments of the invention, only. Hence, the invention is not restricted neither by the subsequent description of the preferred embodiments not by the reference to the Figures nor by the Figures itself.

Figures Legends

DETAILED DESCRIPTION OF THE INVENTION

Figure 1:
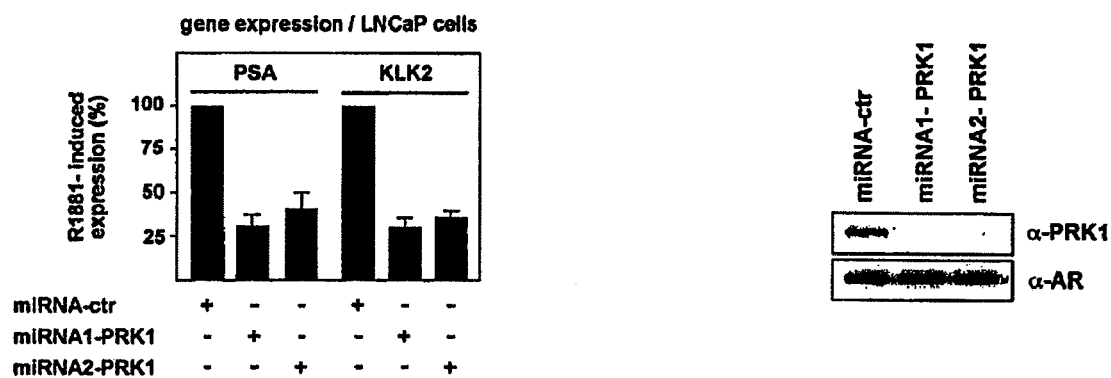
FIG. 1: PRK1 controls AR-dependent gene expression and associates with chromatin. LNCaP cells were cultivated in the presence or absence of the AR agonist R1881. miRNA-mediated PRK1 knockdown (a) or the PRK1 inhibitor Ro318220 (b) reduce expression of the endogenous PSA and KLK2 genes (a, left panel, b). Western blot analysis (a, right panel) verified the specific miRNA-mediated knockdown of PRK1. Bars represent mean+SD (n>4). ChIP and Re-ChIP (c) using the indicated antibodies demonstrate androgen-dependent association of PRK1 at promoters of AR-regulated genes. The precipitated chromatin was amplified by PCR using primers flanking the AREs in the promoter region of the PSA and KLK2 genes, or the promoters of the unrelated GAPDH and U6 genes.
Figure 1:
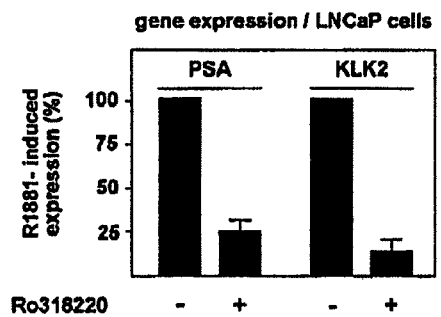
Figure 1:
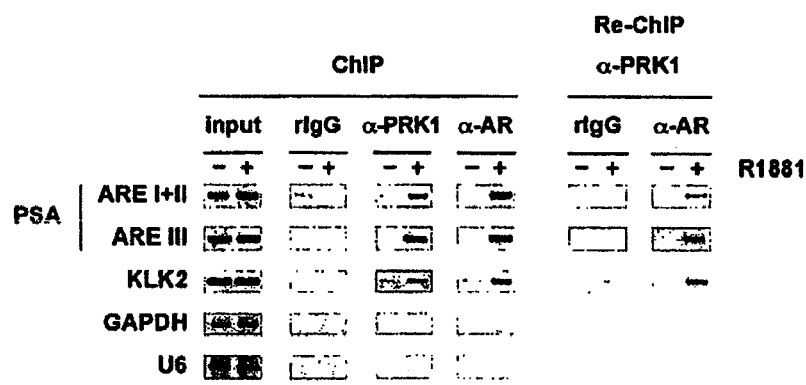

The invention is further described in detail by referring to the Figures.

By the processes of the invention, at least one androgen receptor-regulated (AR-regulated) mechanism in mammalian cells is controlled under histone-phosphorylating conditions. Such AR-regulated mechanisms are numerous in the mammalian body (which is the main, but not exclusive target of the present invention, since all processes of the invention are considered as occurring either in vivo or in vitro) and are well-known to a person skilled in the present field. Preferred (although not exclusive) embodiments of AR-regulated mechanisms in mammalian cells are all physiological processes controlled by the androgen receptor (AR), such as processes selected from the group consisting of the androgen receptor-controlled gene expression and the androgen-induced cell proliferation and the androgen-induced function of the prostate and the androgen-induced build-up of muscles and the androgen-induced build-up of the bones, preferably the androgen-induced control of the bone density, and the androgen-induced fertility and the androgen-induced hair growth of a mammal.

In this connection, the term "mammal" has the meaning of covering all animals (including humans) which nourish the progeny by lactation. The invention is not restricted to humans and includes other mammals as, for example, cattle, horses, monkeys, dogs, cats, rabbits etc.

The term "under histone-phosphorylating conditions", as used in the specification and claims, means that the mammalian cells under observation are kept in a state where modifications of histones by condensation reactions at certain residues with phosphorus-containing residues, particularly with phosphate residues, can be carried out under biologically acceptable conditions or conditions comparable to biological conditions and optionally in the presence of suitable catalysing enzymes. Preferably, the phosphorylation occurs at histone H3 at threonine 11 (H3T11).

The process of the invention for controlling at least one androgen receptor-regulated mechanism in mammalian cells under histone-phosphorylating conditions at histone H3 at threonine 11 (H3T11) comprises the step of allowing at least one inhibitor with specificity for at least one protein kinase C-related kinase (PRK) to act on said at least one PRK. There may be used one inhibitor, or there may be used two or several inhibitors. The use of one inhibitor is preferred in accordance with the invention.

In a preferred embodiment of the invention, the specificity of the inhibitor or inhibitors used towards the at least one protein kinase C-related kinase (PRK) is high. In particularly preferred embodiments of the invention, the at least one inhibitor is a highly specific PRK inhibitor and, more preferably has a specificity of <100 nM. Particularly preferred embodiments of the invention relate to at least one inhibitor or exactly one inhibitor having a specificity of, for example 10 nM.

In more preferred embodiments, said at least one inhibitor or the one inhibitor with high specificity towards at least one PRK is selected from the group consisting of RNAis, antibodies, other peptides and dominant negative mutants of PRKs. Most preferably, said at least one inhibitor or the one inhibitor with high specificity towards at least one PRK is selected from the group consisting of miRNA, sRNA, microRNA, shRNA, anti-PRK1 antibodies and aptamers (i.e. small peptides attaching to the protein and inactivating it; the length of such aptamers may be about 10 peptides, without restricting this term to said length), as well as chemical compounds known to a skilled person to inhibit at least one PRK or several PRKs.

As already mentioned above, the process of the invention for controlling at least one AR-regulated process, in mammalian cells under histone-phosphorylating conditions at H3T11 may be performed in vitro or in vivo. By said process, the activity of said at least one PRK, preferably the activity of exactly one PRK, is modulated. The term "modulation", as used in the present description and in the claims, means any change in the activity of the enzyme, either accelerating or decelerating. In preferred embodiments of the invention, the PRK activity is modulated in the sense of a down-regulation, i.e. in the sense of a deceleration of the kinase reaction whereby, in specific and preferred cases, the PRK-catalysed (at least one) androgen receptor-regulated mechanism in the mammalian cell is blocked.

The at least one inhibitor to act on said at least one PRK may act, in the process of the invention, on any PRK known to a skilled person to be suitable for the desired purposes. In preferred embodiments of the invention, the PRK is selected from the group consisting of PRK1, PRK2 and PKNβ and, most preferably, is PRK1.

The invention is also directed to the use of at least one inhibitor with specificity for at least one protein kinase C-related kinase (PRK) for the manufacture of a medicament for controlling at least one androgen receptor- (AR-) regulated mechanism in mammalian cells.

The term "medicament" is understood in the present description and claims to mean pharmaceutically effective agents or compositions (the latter comprising, in addition to the pharmaceutically effective agent, additional effective agents and/or auxiliary substances as, for example, fillers, solvents, coatings and other well known auxiliary substances) having a preventing or therapeutic effect on at least a part (e.g. a cell or a group of cells) of the mammalian body, as well as substances and compositions which may be used for diagnostic or other medically helpful purposes, for example (in the present case) for the scoring and evaluation of certain cells (or of their health status). One example is the scoring of prostate carcinoma cells.

With respect to the term "controlling at least one AR-regulated mechanism in a mammalian cell", reference is made to the above explanation which is included here by reference.

In the use of the invention, said at least one inhibitor being specific for at least one protein kinase C-related kinase is selected from the group consisting of PRK1, PRK2, and PKNβ and most preferably is PRK1.

In a specifically preferred embodiment of the invention, the use of the at least one inhibitor having specificity, preferably high specificity, for at least one PRK is a use for the manufacture of a medicament for preventing and/or treating prostate cancer.

In accordance with the present invention, there is also provided a process for controlling the androgen dependent gene expression induced by a phosphorylation of histone H3 at threonine 11 (H3T11) in the presence of at least one protein kinase C-related kinase (PRK). Said process comprises the step of allowing at least one inhibitor with specificity for at least one protein kinase C-related kinase (PRK) to act on said at least one PRK, thereby modulating, preferably down-regulating, the activity of said at least one PRK and optionally blocking said androgen dependent gene expression.

Also in accordance with the present invention, there is provided a process for controlling the androgen dependent gene expression induced by a demethylation of histone H3 at lysine 9 (H3K9) in the presence of at least one protein kinase C-related kinase (PRK). Said process comprises the step of allowing at least one inhibitor with specificity for at least one protein kinase C-related kinase (PRK) to act on said at least one PRK, thereby modulating, preferably down-regulating, the activity of said at least one PRK and optionally blocking said androgen dependent gene expression.

Also in accordance with the present invention, there is provided a process for controlling the androgen dependent gene expression induced by an acetylation of histone H3 at lysine 9 (H3K9) and/or histone H3 at lysine 14 (H3K14) in the presence of at least one protein kinase C-related kinase (PRK). Said process comprises the step of allowing at least one inhibitor with specificity for at least one protein kinase C-related kinase (PRK) to act on said at least one PRK, thereby modulating, preferably down-regulating, the activity of said at least one PRK and optionally blocking said androgen dependent gene expression.

Also in accordance with the present invention, there is also provided a process for controlling the androgen dependent gene expression induced by a transition from the pre-initiation to the initiation complex which is characterized by a phosphorylation of RNA polymerase II at serine 5 in the C-terminal repeat domain (S5-pCDTpol II) in the presence of at least one protein kinase C-related kinase (PRK). Said process comprises the step of allowing at least one inhibitor with specificity for at least one protein kinase C-related kinase (PRK) to act on said at least one PRK, thereby modulating, preferably down-regulating, the activity of said at least one PRK and optionally blocking said androgen dependent gene expression.

In all of the above processes, there may be used one inhibitor, or there may be used two or several inhibitors. The use of one inhibitor is preferred in accordance with the invention.

In a preferred embodiment of the invention, the specificity of the inhibitor or inhibitors used towards the at least one protein kinase C-related kinase (PRK) is high. In particularly preferred embodiments of the invention, the at least one inhibitor is a highly specific PRK inhibitor and, more preferably has a specificity of <100 nM. Particularly preferred embodiments of the invention relate to at least one inhibitor or exactly one inhibitor having a specificity of, for example 10 nM.

In more preferred embodiments, said at least one inhibitor or the one inhibitor with high specificity towards at least one PRK is selected from the group consisting of RNAis, antibodies, other peptides and dominant negative mutants of PRKs. Most preferably, said at least one inhibitor or the one inhibitor with high specificity towards at least one PRK is selected from the group consisting of miRNA, siRNA, microRNA, shRNA, anti-PRK1 antibodies and aptamers, as well as chemical compounds known to a skilled person to inhibit at least one PRK or several PRKs.

As already mentioned above, the process of the invention for controlling the transcriptional AR activation in mammalian cells under histone H3 at threonine T 11- (H3T11-) phosphorylating conditions may be performed in vitro or in vivo. By said process, the activity of said at least one PRK, preferably the activity of exactly one PRK, is modulated.

The term "modulation", as used in the present description and in the claims, means any change in the activity of the enzyme, either accelerating or decelerating. In preferred embodiments of the invention, the PRK activity is modulated in the sense of a down-regulation, i.e. in the sense of a deceleration of the kinase reaction whereby, in specific and preferred cases, the PRK-catalysed (at least one) androgen receptor-regulated mechanism in the mammalian cell is blocked.

The at least one inhibitor to act on said at least one PRK may act, in the process of the invention, on any PRK known to a skilled person to be suitable for the desired purposes. In preferred embodiments of the invention, the PRK is selected from the group consisting of PRK1, PRK2 and PKNβ.

According to the invention, it is preferred that said modulation, preferably said down-regulation, of a PRK activity, for example of PRK1 activity, results into a modulation, preferably into an inhibition, of the H3T11 phosphorylation, and/or into a modulation, preferably into an inhibition, of the H3K9 demethylation, preferably of the trimethyl-H3K9 and/or of the dimethyl-H3K9 and/or of the monomethyl-H3K9, and/or into a modulation, preferably into an inhibition, of the H3K9 and/or H3K14 acetylation, and/or a modulation, preferably an inhibition, of the transition from the pre-initiation to the initiation complex by a phosphorylation of RNA polymerase II at serine 5 in the C-terminal repeat domain (S5-pCDTpol II). All processes, i.e. phosphorylation, demethylation, acetylation and RNA polymerase transition, result into the same route, i.e. an activation of the process.

In a further preferred embodiment of the present invention, said modulation, preferably down-regulation, of a PRK activity results into a modulation, preferably an inhibition, of H3K9 demethylation by at least one histone demethylase, preferably by LSD1 and by at least one JMJD, specifically by JMJD2C, each alone or both in combination.

There may be used one histone demethylase or there may be used two or more histone demethylases. Most preferably, there is used one histone demethylase. Histone demethylases are known to a skilled person, and most of them are suitable for the purposes of the invention. Most preferably and advantageously, the histone demethylase is lysine specific demethylase (LSD1)[5].

There may be used one JMJD, or there may be used two or several JMJD's; most preferably, the invention uses one JMJD. Several of them are known to a skilled person which may be suitable, e.g. JMJD2A, JMJD2B, JMJD2C etc. In accordance with the invention, there is used JMJD2C, which was recognized recently[4] to demethylate trimethyl-H3K9 to dimethyl-H3K9; in contrast, LSD1 demethylates dimethyl-H3K9 to monomethyl-H3K9 and monomethyl-H3K9 to unmethylated H3K9.

In preferred embodiments of the invention, LSD1 and JMJD2C may be used each alone or both in combination.

Together with the above embodiment or alternatively to the above embodiment, said down-regulation of a PRK activity results into a modulation, preferably an inhibition, of the H3K9 acetylation and/or H3K14 acetylation by acetylases. There may be used generally known acetylases, and in accordance with the invention, acetylases as, for example, P300/CBP or TIP60 are preferred.

The above processes for controlling the androgen dependent gene expression induced by a phosphorylation of H3T11 in the presence of at least one PRK and/or for controlling the androgen dependent gene expression induced by a demethylation of H3K9 in the presence of at least one PRK and/or for controlling the androgen dependent gene expression induced by an acetylation of H3K9 and/or H3K14 in the presence of at least one PRK and/or for the androgen dependent gene expression induced by the transition from the pre-initiation to the initiation complex by a phosphorylation of RNA polymerase II at serine 5 in the C-terminal repeat domain (S5-pCDTpol II) in the presence of at least one PRK may be performed in vivo or in vitro. In further preferred embodiments of the invention, said at least one PRK, more preferably said one PRK, is selected from PRK1, PRK2 or PKNβ and, utmost preferred, is PRK1.

The invention also relates to the use of at least one inhibitor with specificity for at least one protein kinase C-related kinase (PRK) for the manufacture of a medicament for controlling the androgen dependent gene expression induced by a phosphorylation of H3T11 in the presence of at least one protein kinase C-related kinase (PRK) and/or relates to the use of at least one inhibitor with specificity for at least one protein kinase C-related kinase (PRK) for the manufacture of a medicament for controlling the androgen dependent gene expression induced by a demethylation of histone H3 at lysine 9 (H3K9) in the presence of at least one protein kinase C-related kinase (PRK) and/or relates to the use of at least one inhibitor with specificity for at least one protein kinase C-related kinase (PRK) for the manufacture of a medicament for controlling the androgen dependent gene expression induced by an acetylation of histone H3 at lysine 9 (H3K9) and/or histone H3 at lysine 14 (H3K14) in the presence of at least protein kinase C-related kinase (PRK) and/or relates to the use of at least one inhibitor with specificity for at least one protein kinase C-related kinase (PRK) for the manufacture of a medicament for controlling the androgen dependent gene expression induced by the transition from the pre-initiation to the initiation complex by a phosphorylation of RNA polymerase II at serine 5 in the C-terminal repeat domain (S5-pCDTpol II) in the presence of at least one protein kinase C-related kinase (PRK). Also in connection to the above uses, the preferred embodiments of the invention are the same as mentioned above, and reference is made to the above detailed explanations.

Particularly preferred is the use of said at least one inhibitor, more preferably of said one inhibitor, with specificity for at least one PRK for the manufacture of a medicament for preventing and/or treating prostate cancer.

Additionally, the invention relates to a process for the prevention and/or treatment of prostate cancer, said process comprising administering, to one or a to plurality of mammalian cell(s) in need thereof, including prostate cancer cells in need thereof, at least one inhibitor with specificity for at least one protein kinase C-related kinase (PRK). There may be administered one inhibitor, or there may be administered two or several inhibitors. Preferred is the administration of one inhibitor.

By such an administration, there is modulated, preferably there is down-regulated, the phosphorylation of histone H3 at threonine 11 (H3T11) by said at least one PRK and/or there is modulated, preferably there is down-regulated, the demethylation of histone H3 at lysine 9 (H3K9) by at least one histone demethylase, preferably by lysine specific demethylase (LSD1) and/or by at least one JMJD, and specifically by JMJD2C, each alone or both in combination, and/or there is modulated, preferably there is down-regulated, the acetylation of histone H3 at lysine 9 (H3K9) and/or of histone 3 at lysine 14 (H3K14) by at least one acetylase and/or there is modulated, preferably there is down-regulated, the transition from the pre-initiation to the initiation complex by a phosphorylation of RNA polymerase II at serine 5 in the C-terminal repeat domain (S5-pCDTpol II).

One inhibitor with specificity, preferably with high specificity, towards at least one PRK may be used, or two or several inhibitors may be used. The use of one inhibitor is preferred in accordance with the invention.

In a preferred embodiment of the invention, the specificity of the inhibitor or inhibitors used towards the at least one protein kinase C-related kinase (PRK) is high. In particularly preferred embodiments of the invention, the at least one inhibitor is a highly specific PRK inhibitor and, more preferably has a specificity of <100 nM. Particularly preferred embodiments of the invention relate to at least one inhibitor or exactly one inhibitor having a specificity of, for example 10 nM.

In more preferred embodiments, said at least one inhibitor or the one inhibitor with high specificity towards at least one PRK is selected from the group consisting of RNAis, antibodies, other peptides and dominant negative mutants of PRKs. Most preferably, said at least one inhibitor or the one inhibitor with high specificity towards at least one PRK is selected from the group consisting of miRNA, sRNA, microRNA, shRNA, anti-PRK1 antibodies and aptamers, as well as al chemical compounds known to a skilled person to be inhibitors of at least one PRK, specifically of PRK1.

As already mentioned above, the process of the invention for preventing and/or treating cancer in mammalian cells and particularly prostate cancer may be performed in vitro or in vivo. By said process, the activity of said at least one PRK, preferably the activity of exactly one PRK, is modulated.

The invention also relates to the use of at least one inhibitor with specificity, preferably with high specificity, for at least one protein kinase C-related kinase (PRK), more preferably for exactly one PRK, for the manufacture of a medicament for the prevention and/or treatment of prostate cancer.

The medicaments addressed above may be medicaments for any desirable administration route, for example the oral, enteral, intramuscular, intravenous, parenteral, and other known administration routes. The medicaments may be in any form suitable for the desired administration route, e.g. in the form of tablets, lozenges, dragees, solutions, suspensions and other known administration or dosage forms, including those containing two components for simultaneous administration and/or effect or for simultaneous administration for successive (including sustained) effect or for successive administration for simultaneous or successive (including sustained) effect.

The invention also relates to the use of at least one antibody with specificity for at least one protein kinase C-related kinase (PRK) for the manufacture of a composition, for example an assay system, capable of scoring prostate carcinomas. Such an assay system is considered to be capable to supplement, increase the reliability of and, in future, replace the state of the art Gleason scoring system used for scoring a prostate cancer tissue differentiation and malignancy grade.

The corresponding assay system comprises as the minimum components at least one PRK-specific antibody, the substrate (which usually is the tissue sample to be investigated physiologically) as well as auxiliary agents as, for example, buffers and pH value-adjusting agents, said auxiliary agents being well known to a skilled person and being at his disposition in accordance with the specific assay to be performed.

Figure 2:
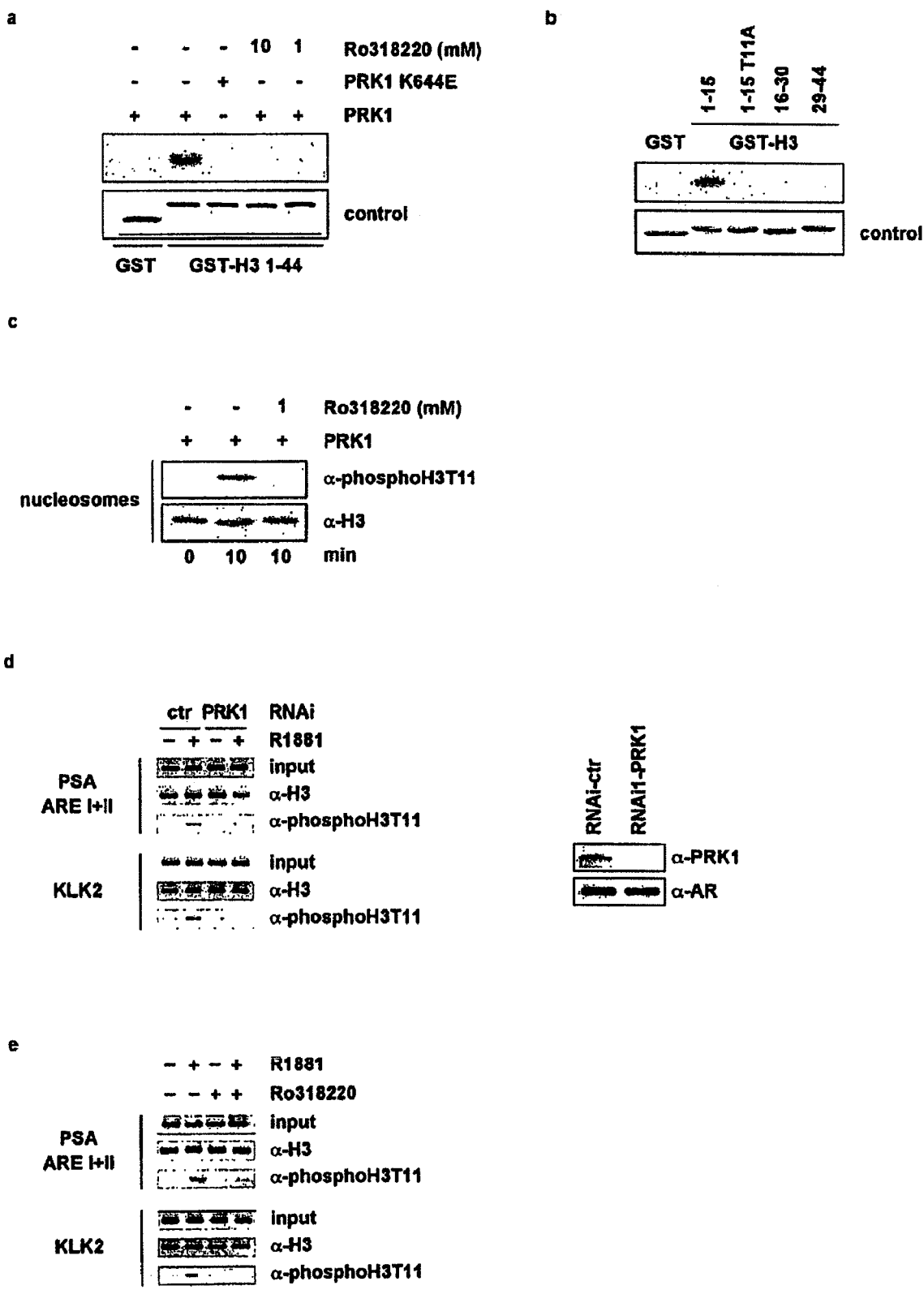
FIG. 2: PRK1 phosphorylates histone H3 at threonine 11 (H3T11). Bacterially expressed GST and GST-H3 fragments (a, b) or nucleosomes from HeLa cells (c) were incubated for the indicated time with active PRK1 or the kinase dead mutant PRK1 K644E in the presence or absence of the inhibitor Ro318220. Coomassie blue staining shows the amounts of GST fusion proteins used (a and b, lower panels). Western blots were decorated with the indicated antibodies (c). LNCaP cells (d, e) were cultivated in the presence or absence of the AR agonist R1881, transfected with stealth RNAi, and subjected to ChIP with the indicated antibodies. The precipitated chromatin was amplified by PCR using primers flanking AREs in the promoter region of the PSA and KLK2 genes. Western blot analysis (d, right panel) verified the specific siRNA-mediated knockdown of PRK1.
Figure 3:
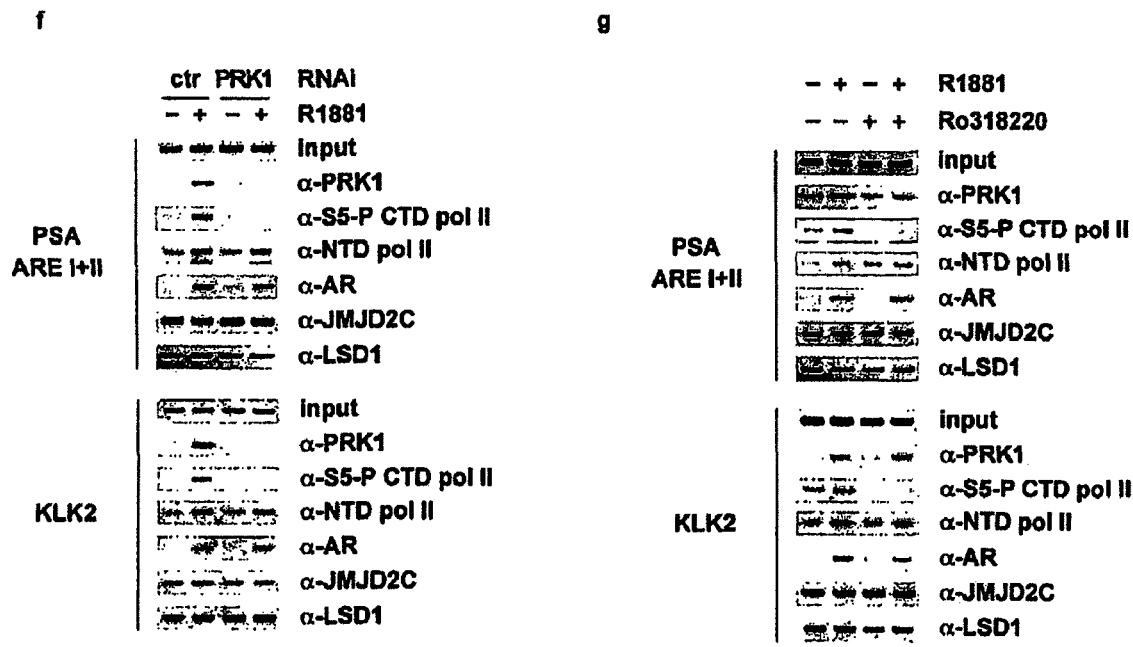
FIG. 3: PRK1 controls epigenetic modifications of histone H3 and AR-dependent gene expression. For ChIP (a, b, f, g) and transient transfections (c, d, e), cells were cultivated in the presence or absence of the AR agonist R1881 and the inhibitor Ro318220 as indicated. LNCaP cells were transfected with stealth RNAi (a, f). ChIP analyses were performed with the indicated antibodies. The precipitated chromatin was amplified by PCR using primers flanking AREs in the promoter region of the PSA and KLK2 genes. For transient transfections, CV1 (c, e) or 293 (d) cells were co-transfected with AR expression plasmid and AR-dependent reporters. Bars represent mean+SD (n>4).
Figure 4:
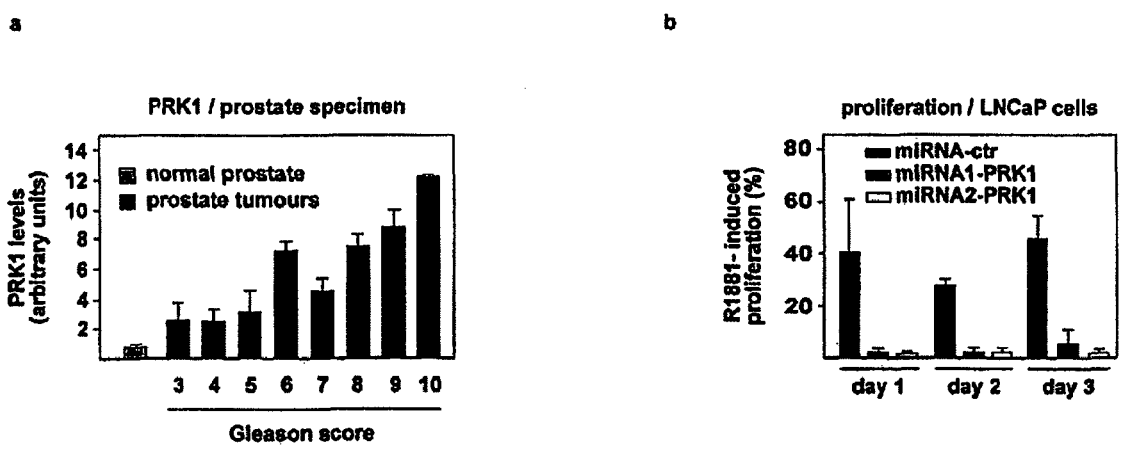
FIG. 4: PRK1 levels positively correlate with the malignancy of prostate cancer and control tumour cell proliferation. The correlation of high PRK1 expression with high Gleason score in a panel of 111 human prostate carcinomas is highly significant: $r=0.499$, $p<0.001$. Normal prostate specimens ($n=20$) are included as a control (a). In LNCaP cells, miRNA-mediated PRK1 knockdown severely reduces R1881-induced cell proliferation. Bars represent mean+SD (n>4) (b).
Figure 5:
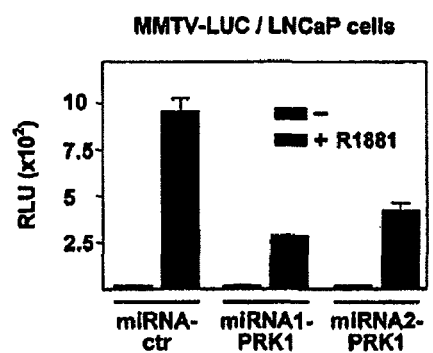
FIG. 5: PRK1 controls AR-dependent gene expression. LNCaP cells were cultivated in the presence or absence of the AR agonist R1881. miRNA-mediated PRK1 knockdown (a) or the inhibitor Ro318220 (b) severely reduce AR-dependent reporter activity. Bars represent mean+SD (n>4).
Figure 5:
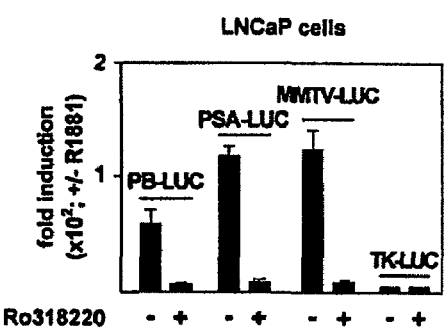

The invention also relates to an assay for screening inhibitors having specificity for at least one PRK capable of blocking AR-induced prostate carcinoma cell proliferation, said assay comprising one or more than one of the following (optionally consecutive) steps:

conducting kinase assays for screening for specific PRK inhibitors, particularly for specific PRK1 inhibitors; an example of such kinase assays is described below, and the results are presented in FIGS. 2a, 2b, and 2c;

conducting chromatin immunoprecipitation tests (chip) in order to learn whether the inhibitors identified in the previous step modulate, down-regulate or even block (inhibit) a PRK-mediated (particularly PRK1-mediated)

phosphorylation at histone H3 at threonine 11 (H3T11) at androgen receptor-regulated (AR-regulated) target genes; the results of such a test are exemplarily shown in FIG. 2e;

verifying the inhibition of androgen receptor (AR) transcriptional activity by the PRK inhibitors (specifically PRK1 inhibitors) identified in the previous steps; examples of this step are shown in FIGS. 3c and 3d as well as in the FIG. 5b;

conducting a test of PRK inhibitors, specifically the PRK1 inhibitors, identified in the previous steps for a modulation, preferably a down-regulation or even a blocking of androgen-induced tumour cell proliferation inhibitor; examples of such a test are shown in FIG. 4b.

By such an assay comprising a sequence of tests, inhibitors having specificity for at least one PRK, specifically PRK1, capable of blocking AR-induced prostate carcinoma cell proliferation could easily be identified, and such tests could suitably be performed as an animal model.

The invention is now in detail further described in connection to the experiments performed by the inventors.

To initiate our study, we analysed the effect of PRK1 knockdown on the expression of endogenous AR target genes. LNCaP prostate tumour cells were transduced with lentiviruses expressing miRNAs directed against PRK1, which results in an efficient and specific down-regulation of endogenous PRK1 (FIG. 1a, right panel).

Quantitative RT-PCR analyses demonstrate that the reduction of PRK1 levels strongly impairs androgen-induced expression of endogenous AR target genes such as Prostate Specific Antigen (PSA) or Kallikrein 2 (KLK2) (FIG. 1a, left panel). In addition, treatment with the PRK1 inhibitor Ro318220[2] severely impedes androgen-induced expression of AR target genes, showing that the kinase activity of PRK1 is essential for AR function (FIG. 1b). Similarly, miRNA-mediated knockdown of PRK1 or treatment with Ro318220 results in a strong decrease in ligand-induced expression of various AR-dependent reporters (FIG. 5a, b).

To investigate whether PRK1 associates with chromatin in vivo, LNCaP cells were subjected to chromatin immunoprecipitation (ChIP) in the presence or absence of the AR agonist R1881. PRK1 associates with the androgen response elements (AREs) located in the promoters of the PSA and KLK2 genes in a ligand-dependent manner (FIG. 1c, left panel). Recruitment of PRK1 to chromatin is specific since DNA corresponding to the promoters of the unrelated GAPDH and U6 genes is not enriched.

To show that PRK1 and AR are present in the same complex on the PSA and KLK2 promoters, R1881-treated LNCaP cells were subjected to sequential chromatin immunoprecipitation (Re-ChIP), first with an α-AR and then with an α-PRK1 antibody. Importantly, the ARE-containing regions are specifically enriched, demonstrating that PRK1 and AR form a complex on chromatin in a ligand-dependent manner (FIG. 1c, right panel).

Figure 6:
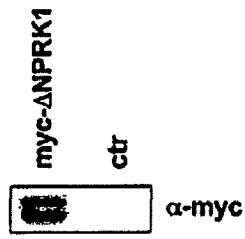
FIG. 6: In 293 cell lysates, the presence of PRK1 proteins used for the kinase assay was verified by Western blot analysis using an α-myc (a) or an α-flag (b) antibody.
Figure 6:
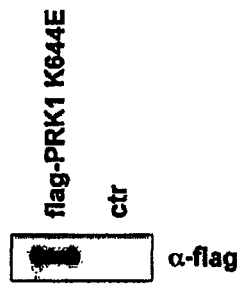

To understand how association of PRK1 and AR with chromatin results in increased gene expression, we tested whether PRK1 directly phosphorylates the N-terminal tail of histone H3. Myc-PRK1 and the flag-tagged kinase dead mutant PRK1 K644E[2] were immunoprecipitated from 293 cell lysates with an α-myc or an α-flag antibody, respectively (FIG. 6a, b), and incubated with bacterially expressed and purified GST-H3 1-44 or GST control protein. GST-H3 1-44 is phosphorylated by PRK1, but not by PRK1 K644E (FIG. 2a). The GST control protein is not phosphorylated, thus demonstrating specificity. Furthermore, addition of Ro318220 completely blocks the phosphorylation of GST-H3 1-44 by PRK1 (FIG. 2a).

Figure 7:
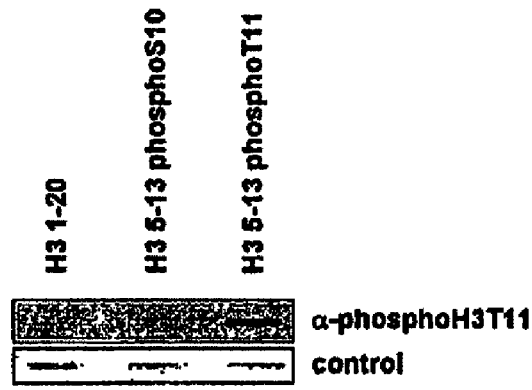
FIG. 7: The α-phosphoH3T11 antibodies used for Western blot analysis (a) and for ChIP assays (b) specifically recognize H3 phosphoT11. 1 μg of the indicated peptide was spotted onto nitrocellulose (Protran BA 79, Schleicher & Schuell). The H3 1-20 peptide was obtained from Peptides & Elephants. The H3 5-13 phosphoS10 and H3 5-13 phosphoT11 peptides were obtained from Abcam. Western blots were decorated as indicated. Controls show equal amounts of Ponceau red stained peptides (a, b, lower panels).
Figure 7:
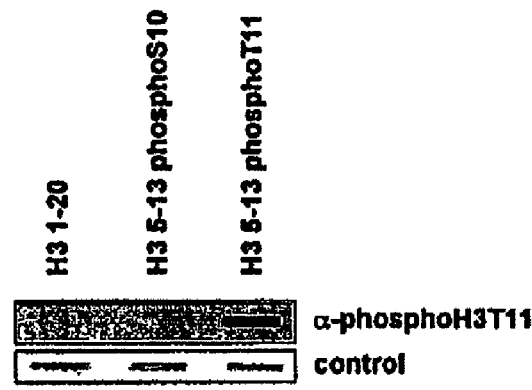

Deletion mapping revealed that only the fragment of histone H3 spanning amino acid residues 1 to 15 (H3 1-15), but not H3 16-30 or H3 29-44, is phosphorylated by purified recombinant PRK1 (FIG. 2b). More importantly, mutation of threonine 11 to alanine in H3 1-15 (H3 1-15 T11A) abolishes phosphorylation, demonstrating that PRK1 targets histone H3 at threonine 11 (H3T11) (FIG. 2b). In addition, we incubated nucleosomes purified from HeLa cells with recombinant PRK1 in the presence or absence of Ro318220. Western blot analysis, performed with an α-phosphoH3T11 specific antibody (FIG. 7a) demonstrates that PRK1 phosphorylates nucleosomes at H3T11 (FIG. 2c). This phosphorylation is blocked by Ro318220 (FIG. 2c).

To determine whether PRK1 controls phosphorylation of H3T11 at promoters of AR-regulated genes in vivo, LNCaP cells were first transfected with either an unrelated control siRNA or a siRNA directed against PRK1, in the presence or absence of R1881, and then subjected to ChIP. Addition of ligand results in phosphorylation of H3T11 at the AREs of the PSA and KLK2 promoters (FIG. 2d, left panel). Androgen-induced phosphorylation at H3T11 is PRK1-dependent since it is blocked by knockdown of PRK1. PRK depletion is specific and does not affect the levels of endogenous AR (FIG. 2d, right panel). To corroborate that androgen-induced phosphorylation of H3T11 is executed by PRK1, LNCaP cells were cultivated in the presence or absence of Ro318220 and subjected to ChIP. As expected, Ro318220 efficiently blocks ligand-induced phosphorylation of H3T11 (FIG. 2e).

Taken together, these data demonstrate that PRK1 phosphorylates H3T11. Importantly, the phosphorylation of H3T11 associates with AR-dependent gene expression, thus introducing phosphorylated H3T11 as a novel epigenetic mark for transcriptional activation.

Since ligand-dependent expression of AR target genes demands removal of repressive methyl marks from H3K9[4, 5] and acetylation of histone H3K9/K14[6], we analysed whether PRK1 controls changes in these epigenetic marks. Therefore, LNCaP cells cultivated in the presence or absence of R1881 were transfected with either an unrelated control siRNA or a siRNA directed against PRK1 and subjected to ChIP. Ligand-induced demethylation of tri-, di-, and monomethyl H3K9 at the AREs of the PSA and KLK2 promoters is severely impaired by PRK1 knockdown (FIG. 3a). Furthermore, ligand-induced acetylation of H3K9/K14 is also blocked (FIG. 3a). Similarly, inhibition of PRK1 activity by Ro318220 results in loss of demethylation of H3K9 and acetylation of H3K9/K14 (FIG. 3b), providing evidence that the kinase activity of PRK1 is pivotal in controlling these epigenetic alterations at AR target genes.

Figure 8:
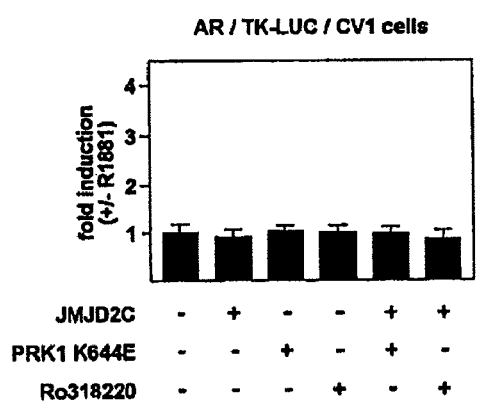
FIG. 8 AR, PRK1 K644E, JMJD2C, and LSD1 do not influence the transcriptional activity of the TK-LUC control reporter. CV1 (a, c) or 293 (b) cells were co-transfected with expression plasmids and the TK-LUC reporter in the presence or absence of R1881 and Ro318220, as indicated. Bars represent mean+SD (n>4).
Figure 8:
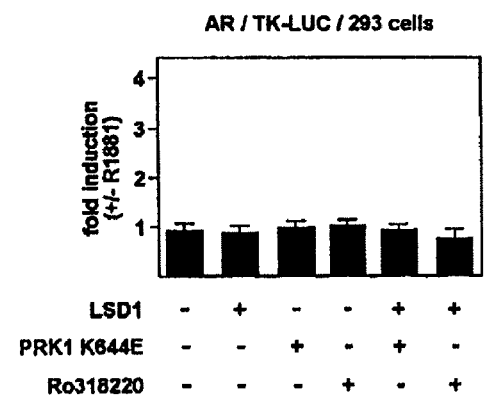
Figure 8:
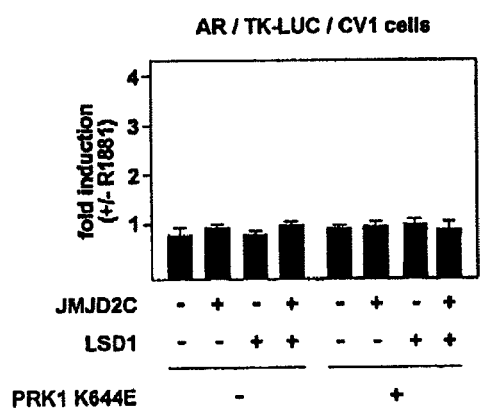

As previously shown, JMJD2C[4] and LSD1[5] remove repressive methyl marks from H3K9 during AR-dependent transcription. Since PRK1 controls demethylation of H3K9, we investigated the interplay between PRK1 and the demethylases during gene expression in transient transfections. Co-expression of AR with either JMJD2C (FIG. 3c and ref[4]) or LSD1 (FIG. 3d and ref[5]) results in a strong ligand-dependent activation of the PSA-LUC or MMTV-LUC reporters. Co-activation by the demethylases is abrogated by PRK1 K644E, acting as a dominant negative mutant, or by treatment with Ro318220. To examine the effect of PRK1 K644E on co-operative stimulation of AR activity by JMJD2C and LSD1, we expressed both demethylases in limited amounts, which alone do not activate AR, but together induce a strong AR superactivation[4]. As shown in FIG. 3e. PRK1 K644E blocks co-operative stimulation of AR activity. The control reporter TK-LUC is not affected by PRK1 (FIG. 8a-c). Collectively, these data demonstrate that PRK1 signaling controls transcriptional activation of AR by the demethylases JMJD2C and LSD1.

Initiation of transcription requires transition from the pre-initiation to the initiation complex, which is characterized by phosphorylation of RNA polymerase II at serine 5 in the C-terminal repeat domain (S5-P CTD pol II) by the CDK7 component of TFIIH[3]. To determine whether depletion or inhibition of PRK1 interfered with the formation of the transcriptional initiation complex at AR-regulated promoters, we performed ChIP using an antibody that specifically recognizes S5-P CTD pol II. Importantly, knockdown of PRK1 or treatment of cells with Ro318220 results in the loss of S5-P CTD pol II at the promoters of PSA and KLK2. In contrast, recruitment of RNA polymerase II is not affected, as shown by ChIP using an antibody directed against the N-terminal domain of RNA polymerase II (α-NTD pol II) (FIG. 3f, g).

Taken together, these data show that PRK1 not only controls changes in epigenetic marks on histone H3, but also regulates the transition from pre-initiation to initiation complex.

To unravel the physiological importance of PRK1, we investigated the levels of PRK1 in vivo by immunostaining a panel of 20 normal human prostates and 111 prostate carcinomas on tissue microarrays. Quantification of immunoreactivity by scoring staining intensity and percentage of positive carcinoma cells[7] reveals that high PRK1 expression significantly correlates with high Gleason scores and indicates aggressive biology of the tumours (FIG. 4a).

Furthermore, to examine whether PRK1 regulates tumour cell proliferation, we monitored androgen-dependent cell growth by quantifying proliferation of pLenti6-miRNA-PRK1-infected LNCaP cells. When compared to cells expressing an unrelated control miRNA, androgen-induced proliferation of LNCaP cells is dramatically reduced by PRK1 knockdown (FIG. 4b), thus underlining the importance of PRK1 in the control of AR-dependent tumour cell growth.

In summary, we demonstrate that phosphorylated H3T11 is a novel epigenetic mark for transcriptional regulation. Phosphorylation of H3T11 is executed by PRK1 in an androgen-dependent manner. By controlling subsequent steps of gene activation such as demethylation of tri-, di-, and monomethyl H3K9, acetylation of H3K9/K14, and the presence of S5-P CTD pol II at target promoters, PRK1 functions as a gatekeeper of AR-regulated gene expression. Of importance is our observation that inhibitors such as Ro318220 control the kinase activity of PRK1 and thereby regulate AR. Thus, specific modulation of PRK1 activity is a promising therapeutic strategy in the treatment of prostate cancer, where AR is pivotal to the control of tumour cell proliferation.

Examples

Plasmids

The following plasmids were described previously: pSG5-AR, pCMX-flag, pCMV-flag-PRK1 K644E, pcDNA3-myc-ΔNPRK1, TK-LUC, MMTV-LUC, Probasin-LUC, and PSA-LUC[2]; pCMX-flag-JMJD2C[4], pCMX-flag-LSD1[5], GST-H3 1-44[8].

To construct pLenti6-miRNA1-PRK1, pLenti6-miRNA2-PRK1, pGW-miRNA1-PRK1, and pGW-miRNA2-PRK1, the DNA corresponding to miRNA1-PRK1 (5'-TGCTGAT-TGCTGTAGGTCTGGATCATGTTTTGGC-CACTGACTGAC ATGATCCACCTACAAT-3' (Sequence Protocol: 1) (SEQ ID NO: 1) and 5'-CCTGATTGCTGTAG-GTGGATCATGTCAGTCAGTGGCCAAAA-CATGATCCAGA CCTACAGCAATC-3') (Sequence Protocol: 2) (SEQ ID NO: 2) and miRNA2-PRK1 (5'-TGCTGTTACTGTCCTGCAACATCTGCGTTTTGGCC-ACTGACTG ACGCAGATGTCAGGACAGTAA-3' (Sequence Protocol: 3) (SEQ ID NO: 3) and (5'-CCTGTTACT-GTCCTGACATCTGCGTCAGTCAGTGGC-CAAAACGCAGATGTTG CAGGACAGTAAC-3') (Sequence Protocol: 4) (SEQ ID NO: 4) was cloned into pLenti6N5-DEST and pcDNA-6.2-GW-EmGFP according to the manufacturer's instructions (Invitrogen). To construct GST-H3 1-15, GST-H3 1-15 T11A, GST-H3 16-30, and GST-H3 29-44, the corresponding cDNA fragments were cloned into pGEX4T1. Cloning details can be obtained upon request.

Cell Culture and Transfection

CV1 and LNCaP cells were cultured and transfected as described[2]. The following amounts were transfected per well: 500 ng of MMTV-LUC, Probasin-LUC, or PSA-LUC; 25 ng of AR expression plasmid; 200 ng (FIG. 3e) or 400 ng (FIG. 3c, d) expression plasmids of LSD1 or JMJD2C, 150 ng PRK1 K644E, 1000 ng expression plasmid of miRNA-control, miRNA1-PRK1, or miRNA2-PRK1 (FIG. 5a). Cells were cultivated for 18 hours in the presence or absence of $1 \times 10^{-10}$ M R1881 (Sigma), $2.5 \times 10^{-6}$ M (FIG. 3d) or $4.5 \times 10^{-6}$ M (FIG. 3c) Ro318220 (Roche) as indicated. Luciferase activity was assayed as described[2]. All experiments were repeated at least four times in duplicate.

Generation of PRK1 Antibody

The polyclonal rabbit-α-PRK1 antibody was generated according to standard procedures.

Chromatin Immunoprecipitation ChIP and Re-ChIP experiments were performed as described[5,9]. LNCaP cells were cultured for 45 min (FIGS. 1c, 2d, 2e) or 210 min (FIG. 3a, b, f, g) in the presence or absence of $1 \times 10^{-8}$ M R1881 as indicated. Ro318220 ($1 \times 10^{-5}$ M) was added to the LNCaP cells (FIG. 3b, g) 60 min before addition of R1881. Three days before harvesting, LNCaP cells were transfected with stealth RNAi (ctr: 5'-GAACAUGAUCCAGACCUACAGCAAU-3' (Sequence Protocol: 5) (SEQ ID NO: 5); PRK1: 5'-GAAAGUCCUAGAUCCACACGCAAAU-3' (Sequence Protocol: 6) (SEQ ID NO: 6); Invitrogen) following the manufacturer's instructions. Immunoprecipitation was performed with specific antibodies (α-monoMeH3K9, α-diMeH3K9, α-triMeH3K9, α-acetyl-H3K9/K14, α-H3, α-AR (Upstate Biotechnology), α-S5-P CTD pol II, α-phosphoH3T11 (Abcam), α-NTD pol II (N-20, Santa Cruz), α-LSD1[5], α-JMJD2C[4], and α-PRK1) on protein A-Sepharose 4B (GE-Healthcare). For PCR, 1-5 µl out of 50 µl DNA extract was used. PCR primers for ARE I+II (PSA-459/-121), ARE III (PSA-4288/-3922), KLK2 (−343/-90), GAPDH, and U6 were described previously[5].

Western Blot Analysis

Experiments were performed as described[2]. Western blots were decorated as indicated.

Cell Proliferation Assay

Experiments were performed as described[5]. pLenti6-miRNA-control, pLenti6-miRNA1-PRK1, and pLenti6-miRNA2-PRK1 were used to produce recombinant lentiviruses to infect LNCaP cells as described[10]. The infected cells were cultured for 72 hours in medium containing 10% double-stripped FCS. $1 \times 10^4$ cells were plated in a 96-well plate in the presence or absence of $1 \times 10^{-9}$ M R1881. The cell proliferation Elisa BrdU Colorimetric Assay (Roche) was performed according to the manufacturer's instructions. The figure shows the percentage increase of proliferation in the presence versus absence of R1881. The experiments were performed in quintuplicate.

Quantitative RT-PCR and Statistical Analysis

Quantitative RT-PCR and statistical analysis were performed as described[5]. The primers for GAPDH, PSA, and KLK2 were described previously[5].

In Vitro Kinase Assay

The kinase assays were performed as described[11]. 10 µg GST-tagged H3 proteins or 1 µg of nucleosomes purified from HeLa cells[12] were incubated with immunoprecipitated PRK1 proteins (FIG. 2a) or 1 µg purified recombinant PRK1 (FIG. 2b, c; ProQinase GmbH) for 0 to 10 min (FIG. 2c) or 20 min (FIG. 2a, b) at 30° C. in kinase buffer containing 20 mM Tris-HCl pH 7.5, 20 µM ATP, 8 mM $MgCl_2$, and 5 µCi ($\gamma$-$^{32}$P) ATP. The reaction mixture was analysed by SDS-PAGE followed by autoradiography or Western blotting using antibodies as indicated.

Statistical Analysis of Tissue Microarrays

Clinical data of patients and procedures for generating the tissue microarrays were described previously[7]. Statistical analysis was performed with the Mann-Whitney U-Test using the SPSS 12.0 program (SPSS Inc.) and by calculating the two-tailed Spearman Rank correlation coefficient. The number of cases (n) analysed per Gleason score (Gs) were: Gs 3 (n=5); Gs 4 (n=12); Gs 5 (n=11); Gs 6 (n=25); Gs 7 (n=16); Gs 8 (n=23), Gs 9 (n=10); Gs 10 (n=9). Normal prostate specimen (n=20).

LITERATURE

1. Strahl, B. D. & Allis, C. D. The language of covalent histone modifications. *Nature* 403, 41-5. (2000).
2. Metzger, E. et al. A novel inducible transactivation domain in the androgen receptor: implications for PRK in prostate cancer. *EMBO J.* 22, 270-80. (2003).
3. Phatnani, H. P. & Greenleaf, A. L. Phosphorylation and functions of the RNA polymerase II CTD. *Genes Dev.* 20, 2922-36. (2006).
4. Wissmann, M. et al. Cooperative demethylation by JMJD2C and LSD1 promotes androgen receptor-dependent gene expression. *Nat. Cell. Biol.* 9, 347-53. (2007).
5. Metzger, E. et al. LSD1 demethylates repressive histone marks to promote androgen-receptor-dependent transcription. *Nature* 437, 436-9. (2005).
6. Kang, Z., Pirskanen, A., Janne, O. A. & Palvimo, J. J. Involvement of proteasome in the dynamic assembly of the androgen receptor transcription complex. *J. Biol. Chem.* 277, 48366-71. (2002).
7. Kahl, P. et al. Androgen receptor coactivators lysine-specific histone demethylase 1 and four and a half LIM domain protein 2 predict risk of prostate cancer recurrence. *Cancer Res.* 66, 11341-7. (2006).
8. Dai, J., Sultan, S., Taylor, S. S. & Higgins, J. M. The kinase haspin is required for mitotic histone H3 Thr 3 phosphorylation and normal meta-phase chromosome alignment. *Genes Dev.* 19, 472-88. (2005).
9. Shang, Y., Myers, M. & Brown, M. Formation of the androgen receptor transcription complex. *Mol. Cell* 9, 601-10. (2002).
10. Wiznerowicz, M. & Trono, D. Conditional suppression of cellular genes: lentivirus vector-mediated drug-inducible RNA interference. *J. Virol.* 77, 8957-61. (2003).
11. Dong, L. Q. et al. Phosphorylation of protein kinase N by phosphoinositide-dependent protein kinase-1 mediates insulin signals to the actin cytoskeleton. *Proc. Natl. Acad. Sci. U.S.A.* 97, 5089-94. (2000).
12. O'Neill, T. E., Roberge, M. & Bradbury, E. M. Nucleosome arrays inhibit both initiation and elongation of transcripts by bacteriophage T7 RNA polymerase. *J. Mol. Biol.* 223, 67-78. (1992).

The invention claimed is:

1. A method of scoring the malignancy of prostate cancer, wherein the method comprises:
   (a) determining a level of PRK1 in a sample of prostate cancer cells by using an antibody specific for PRK1;
   (b) comparing the level of PRK1 determined according to (a) with a level of PRK1 in non-cancerous prostate cells; and
   (c) scoring the malignancy of the prostate cancer based on the comparison of (b), a higher difference between the level of PRK1 in the prostate cancer cells and the level of PRK1 in the non-cancerous cells indicating a higher aggressiveness of the prostate cancer.

* * * * *

SEQUENCE LISTING

```
<160> NUMBER OF SEQ ID NOS: 6

<210> SEQ ID NO 1
<211> LENGTH: 61
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
tgctgattgc tgtaggtctg gatcatgttt tggccactga ctgacatgat ccacctacaa    60
t                                                                    61

<210> SEQ ID NO 2
<211> LENGTH: 64
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
cctgattgct gtaggtggat catgtcagtc agtggccaaa acatgatcca gacctacagc    60
aatc                                                                 64
```

```
<210> SEQ ID NO 3
<211> LENGTH: 64
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
tgctgttact gtcctgcaac atctgcgttt tggccactga ctgacgcaga tgtcaggaca    60
gtaa                                                                 64

<210> SEQ ID NO 4
<211> LENGTH: 64
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
cctgttactg tcctgacatc tgcgtcagtc agtggccaaa acgcagatgt tgcaggacag    60
taac                                                                 64

<210> SEQ ID NO 5
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 5
gaacaugauc cagaccuaca gcaau                                          25

<210> SEQ ID NO 6
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 6
gaaaguccua gauccacacg caaau                                          25
```